(12) United States Patent
Sussman et al.

(10) Patent No.: US 10,736,776 B2
(45) Date of Patent: Aug. 11, 2020

(54) SYSTEMS AND METHODS FOR OCULAR SURGERY

(71) Applicant: Alcon Inc., Fribourg (CH)

(72) Inventors: Glenn Robert Sussman, Laguna Niguel, CA (US); John Morgan Bourne, Irvine, CA (US); John Richard Carpenter, Santa Ana, CA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 16/174,914

(22) Filed: Oct. 30, 2018

(65) Prior Publication Data

US 2019/0060117 A1 Feb. 28, 2019

Related U.S. Application Data

(63) Continuation of application No. 15/280,802, filed on Sep. 29, 2016, now Pat. No. 10,143,588, which is a continuation of application No. 14/929,249, filed on Oct. 30, 2015, now Pat. No. 9,545,336, which is a continuation of application No. 14/191,886, filed on Feb. 27, 2014, now Pat. No. 9,693,896.

(60) Provisional application No. 61/935,595, filed on Feb. 4, 2014, provisional application No. 61/793,840, filed on Mar. 15, 2013.

(51) Int. Cl.
*A61F 9/007* (2006.01)
*A61M 1/00* (2006.01)

(52) U.S. Cl.
CPC ....... *A61F 9/00745* (2013.01); *A61M 1/0064* (2013.01); *A61M 2210/0612* (2013.01)

(58) Field of Classification Search
CPC ............. A61F 9/00745; A61M 1/0064; A61M 2210/0612
See application file for complete search history.

(56) References Cited

U.S. PATENT DOCUMENTS

| 4,764,165 | A | * | 8/1988 | Reimels | A61F 9/00736 604/22 |
| 6,689,146 | B1 | * | 2/2004 | Himes | A61B 17/32002 604/22 |
| 2008/0247892 | A1 | * | 10/2008 | Kawasumi | F04B 43/12 417/476 |
| 2010/0056986 | A1 | | 3/2010 | Allen | |

(Continued)

FOREIGN PATENT DOCUMENTS

| CN | 1348342 A | 5/2002 |
| JP | H06-335523 A | 12/1994 |
| JP | 2009-257179 A | 11/2009 |

(Continued)

*Primary Examiner* — Imani N Hayman (57) ABSTRACT

Ocular surgery may be performed by a variety of systems, processes, and techniques. In certain implementations, systems and processes for ocular surgery may include the ability to emulsify a lens in an eye using a modular hand-held system including a phacoemulsification unit detachably coupled to a pump unit and remove lens portions from the eye using suction provided by the pump unit. The system and the process may also include the ability to decouple the phacoemulsification unit from the pump unit, couple an irrigation-aspiration unit to the pump unit to form a second hand-held system, and remove material from the eye using suction provided by the pump unit.

10 Claims, 4 Drawing Sheets

(56) References Cited

U.S. PATENT DOCUMENTS

2011/0144567 A1* 6/2011 Sorensen ............ A61F 9/00745
604/22

FOREIGN PATENT DOCUMENTS

TW 221374 B 3/1994
TW 200812558 A 3/2008

* cited by examiner

SYSTEMS AND METHODS FOR OCULAR SURGERY

CROSS-REFERENCE TO RELATED APPLICATIONS

This Application is a continuation of prior application Ser. No. 15/280,802, filed Sep. 29, 2016, which is a continuation of prior application Ser. No. 14/929,249, filed Oct. 30, 2015, which is a continuation of prior application Ser. No. 14/191,886, filed Feb. 27, 2014, which claims the benefit of U.S. Provisional Application No. 61/935,595, filed Feb. 4, 2014, and U.S. Provisional Application No. 61/793,840, filed Mar. 15, 2013, the entire contents of each being incorporated herein by reference.

TECHNICAL FIELD

The present disclosure relates to optical surgery, and more specifically to surgical replacement of a patient's lens.

BACKGROUND

The human eye, in simple terms, functions to provide vision by transmitting and refracting light through a clear outer portion called the cornea and focusing the image by way of the lens onto the retina at the back of the eye. The quality of the focused image depends on many factors including the size, shape, and length of the eye, and the shape and transparency of the cornea and lens.

When trauma, age, or disease causes the lens to become less transparent, vision deteriorates because of a reduction in light transmitted to the retina. This deficiency in the eye's lens is medically known as a cataract. The treatment for this condition is often surgical removal of the lens and implantation of an artificial lens, typically known as an intraocular lens (IOL).

An IOL is often foldable and inserted into the eye through a relatively small incision by being advanced through an IOL insertion cartridge, which causes the IOL to fold. The IOL is typically advanced through the insertion cartridge by a plunger-like device.

Before inserting an IOL, the old lens is usually removed through a process called phacoemulsification. In phacoemulsification, an eye's lens is emulsified with an ultrasonic handpiece and aspirated from the eye. Aspirated fluids are replaced with an irrigation of balanced salt solution, thus maintaining the anterior chamber, as well as cooling the handpiece. The irrigation fluid and the aspiration suction are usually supplied by a remote surgical console, which is coupled to the handpiece through several feet of tubing.

Typically, a second stage is required to completely remove the lens, as the first stage only extracts the main portions. Thus, after phacoemulsification, an irrigation-aspiration probe is used to aspirate out the remaining peripheral cortical matter, while leaving the posterior capsule intact.

SUMMARY

A variety of systems, processes, and techniques for ocular surgery are disclosed. In certain implementations, a modular hand-held system for ocular surgery may include a hand-held phacoemulsification unit and a hand-held pump unit. The pump unit may be adapted to provide suction for aspirating fluid and tissue through the phacoemulsification unit and include an adapter configured to detachably couple the phacoemulsification unit to the pump unit to form an integrated hand-held system.

In particular implementations, the phacoemulsification unit is also adapted to receive suction from a surgical console for aspirating material from an eye.

In some certain implementations, the adapter is also configured to detachably couple the pump unit to a handheld irrigation-aspiration unit to form a second integrated hand-held system. The pump unit may also provide suction for aspirating material through the irrigation-aspiration unit.

The phacoemulsification unit may, for example, include a male luer fitting, and the adapter may include a female luer fitting. The luer fittings may, for example, be engaged by a friction fit.

In some implementations, a process for ocular surgery may include emulsifying a lens in an eye using a modular hand-held system including a phacoemulsification unit detachably coupled to a pump unit and removing lens portions from the eye using suction provided by the pump unit. The process may also include decoupling the phacoemulsification unit from the pump unit, coupling an irrigation-aspiration unit to the pump unit to form a second hand-held system, and removing material from the eye using suction provided by the pump unit.

Certain implementations may include polishing a posterior capsule of the eye using the second system.

Various implementations may have one or more features. For example, by using a hand-held system with a local pump unit to remove a diseased lens from an eye, chamber stability may be improved during phacoemulsification. Additionally, since the phacoemulsification unit is detachable from the pump unit, another unit may be coupled to the pump unit. For example, an irrigation-aspiration unit or a vitrectomy unit may be coupled to the pump unit. This provides the ability to use the pump unit for a variety of operations during a procedure, and obtain its advantages in each.

A variety of other features will be apparent to those skilled in the art from the following description and claims, as well as the accompanying drawings.

DETAILED DESCRIPTION

Figure 1:
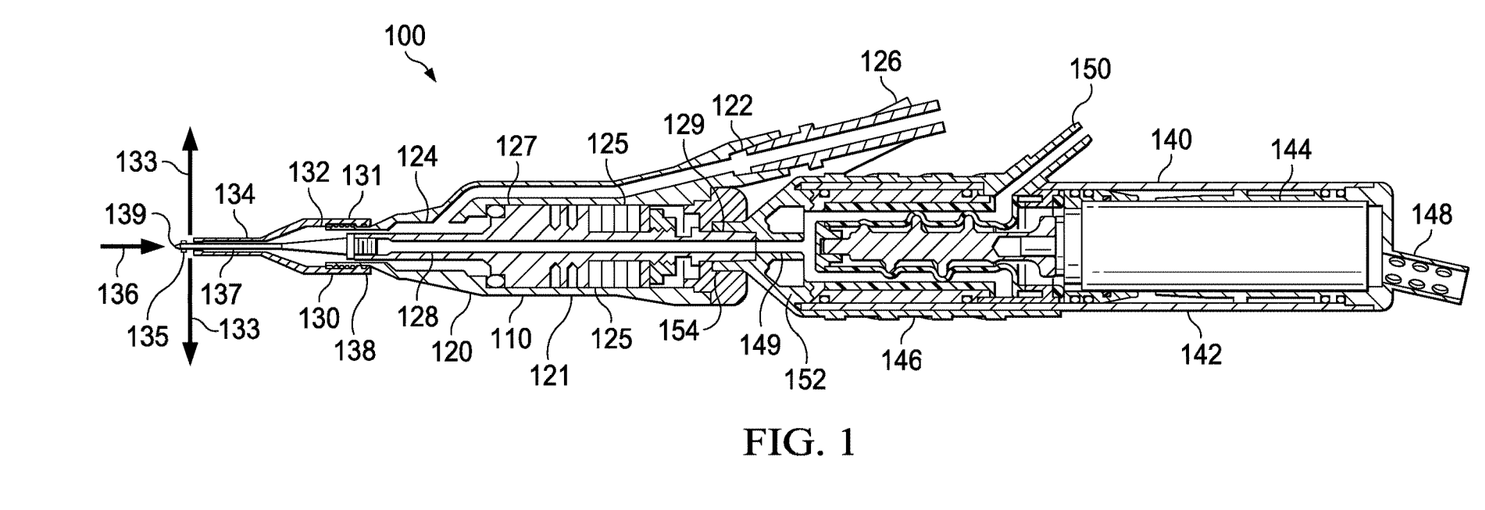
FIG. 1 is a cross-sectional view of an example system for ocular surgery.

FIG. 1 illustrates an example system 100 for ocular surgery. System 100 includes a phacoemulsification unit 110 and a pump unit 140 that are detachably coupled together. In general, phacoemulsification unit 110 is adapted to break up an eye's lens into pieces and aspirate the pieces with the suction provided by pump unit 140.

Phacoemulsification unit 110 includes a body portion 120 and a distal tip assembly 130. Body portion 120 includes a housing 121 that is substantially rigid and may be made of hard plastic, metal, or any other appropriate material. Body portion 120 may be any length. In some implementations, the body portion 120 may have a length between about four to six inches. In other instances, body portion 120 may have a length greater than six inches or smaller than four inches. Body portion 120 also includes an infusion port 122 for receiving infusion fluids (e.g., a water/saline solution) for delivery to an eye during a lens separation and removal process. In some instances, the fluid may, for example, come from a surgical console. Infusion port 122 communicates with a channel 124 inside of housing 121.

Body portion 120 also includes resonators 125. Resonators 125 are adapted to generate high-frequency vibrations (e.g., ultrasonic) in response to applied electrical power, which may be received through an electrical conduit 126. In particular implementations, resonators 125 may be piezoelectric transducers.

Internal to housing 121, body portion 120 includes a horn 127 that is vibrated by resonators 125. Horn 127 may, for example, be composed of metal. Horn 127 includes a channel 128 through which eye fluid and tissue may be aspirated. Horn 127 also includes a male luer fitting 129. In particular implementations, male luer fitting 129 is composed of a polymer, which may facilitate resisting separation due to the vibrations of the system during use.

Distal tip assembly 130 includes a sleeve 131 that is flexible. Sleeve 131 may, for example, be made of an elastomeric material (e.g., silicone). Sleeve 131 forms a channel 132. The channel 132 also communicates with channel 124. Irrigation fluid flows through channel 124 and into channel 132. The fluid may flow through channel 132 until it exits distal tip assembly 130, as indicated by arrows 133.

Distal tip assembly 130 also includes a surgical tip 134. The surgical tip 130 extends through the sleeve 131. Tip 134 is engaged with horn 127 of body portion 120 and receives vibrations from resonators 125 therethrough. Surgical tip 134 may, for example, be made of metal (e.g., stainless steel or titanium). Surgical tip 134 includes a distal section 135 that may be placed against a lens to emulsify it. Particularly, surgical tip 134, when vibrated, is operable to break up and emulsify a natural eye lens. Distal section 135 includes a port 139 into which material from the eye may enter. These materials may include fluid in the eye (e.g., aqueous humor and/or fluid irrigating the eye), lens particles, tissues, and any other material for which removal from the eye is desirable. These materials may be aspirated from the eye, as indicated by arrow 136. The port 139 communicates with a channel 137 that extends through the surgical tip 134. The fluid may be conveyed through channel 137 of the surgical tip 134 and through channel 128 of the horn 127.

In the illustrated implementation, distal tip assembly 130 is adapted to slideably engage body portion 120. For example, a proximal end 152 of surgical tip 134 may be received into a port 154 formed in a distal end 156 of the horn 127. Also, in some instances, a proximal end 158 of sleeve 131 may be received onto a distal end 160 of the housing 121. Further, the proximal end 158 of sleeve 131 may be expandingly flexible at end 138 to receive the distal end 160 of the housing 121.

Pump unit 140 includes a body 142. In some instances, the body 142 may be made of metal, hard plastic, or any other appropriate material. Body 142 may be any length. In some instances, body 142 may have a length about four to six inches. In other instances, body 142 may have a length greater than six inches or smaller than four inches. Body 142 houses, among other things, a motor 144. In some instances, motor 144 may be an electric motor. In other implementations, motor 144 may be other types of motors. For example, in some instances, the motor 144 may be a pneumatic, hydraulic, or any other type of motor operable to operate pump unit 140.

In the present example, an electric motor is described. However, the scope of the disclosure is not so limited, and the description of an electrical motor is provided as an example for illustration purposes only. Motor 144 is operable to produce a rotational drive motion in response to supplied electrical power, which is received through electrical conduit 148. In particular implementations, electric motor 144 may be a direct current (DC) motor. Electric motor 144 may, for example, operate between 0 to 6,000 RPM.

Pump unit 140 also includes a pump 146 that is driven by motor 144. As illustrated, pump 146 is a scroll-type peristaltic pump. In other implementations, pump 146 may be another type of peristaltic pump or any other appropriate type of pump. For example, in some instances, the pump 146 may be a venturi-type pump. Pump 146 draws fluid in through a channel 149, which communicates with channel 128 of phacoemulsification unit 110. Pump unit 140 also includes an aspiration port 150 through which aspirated fluid may be discharged. The aspirated materials (e.g., fluid and tissue, such as aqueous humor, irrigation fluid, cortical material, epithelial cells, etc.) may be conveyed to a container (e.g., a bag or tank).

Pump unit 140 may also include an adapter 152. The adapter 152 may be coupled to a distal end 160 of the pump unit 140. Adapter 152 may include a female luer fitting 154 that is adapted to receive male luer fitting 129 of phacoemulsification unit 110. In some instances, the two luer fittings 129, 154 mate with each with a friction fit. Female luer fitting 154 may, for example, be made of metal (e.g., stainless steel or titanium), plastic, or any other appropriate material.

In operation, one or more incisions are made in the eye to allow the introduction of surgical instruments. A user (e.g., physician or other medical professional) then removes the anterior face of the capsule that contains the lens inside the eye.

Surgical tip 135 of distal tip assembly 130 may then be inserted into the eye through one of the incisions, until tip 135 is in contact with the lens. Resonators 125 may then be activated at a relatively high frequency (e.g., ultrasonic), causing tip 135 to vibrate, to sculpt and emulsify the lens while pump unit 140 aspirates particles through the channel 137 formed in surgical tip 135. Generally, the lens is fragmented into two or four pieces, and each piece is emulsified and aspirated out with suction through channel 137, channel 128, channel 149, and aspiration port 150. After removing all hard portions of a lens, e.g., a central lens nucleus, with phacoemulsification, the softer lens portion, e.g., outer lens cortex, may be removed with suction only (e.g., with an irrigation-aspiration unit).

System 100 has a variety of features. For example, system 100 may be used to remove a diseased lens from an eye. Moreover, locating pump unit 140 nearer to the phacoemulsification unit 110 may improve chamber stability for phacoemulsification. Maintaining a steady intraocular pressure in the eye is important because pressure fluctuations can result in, among other things, posterior capsule rupture, endothelial cell loss, and inflammation. Improved anterior chamber stability should produce improved clinical outcomes. Additionally, since phacoemulsification unit 110 is detachable from pump unit 140, another unit may be coupled to pump unit 140. For example, an irrigation-aspiration probe or a vitrectomy probe may be coupled to the pump unit. Thus, system 100 provides the ability to use pump unit 140 for a variety of operations during a procedure.

Although FIG. 1 illustrates one example system for ocular surgery, other systems for ocular surgery may include fewer, additional, and/or a different arrangement of components. For example, a different phacoemulsification unit may be used with pump unit 140. Thus, pump unit is adaptable to different phacoemulsification units. For instance, in some implementations, a phacoemulsification unit may include a second fine metal instrument called a "chopper" that is used from a side port to help with chopping the nucleus into smaller pieces. As another example, a different pump unit may be used with phacoemulsification unit 110. For example, a different pump unit having an adapter operable to interface with the male luer fitting 129 of the phacoemulsification unit 110 may be used.

As another example, phacoemulsification unit 110 may also be used with a standard surgical console. Because phacoemulsification unit 110 includes male luer fitting 129, it may readily couple to surgical conduits (e.g., hoses or tubes) to a surgical console. That is, in some instances, phacoemulsification unit 110, decoupled from the pump unit 140, may be coupled to a surgical console via one or more surgical conduits.

Although female luer fitting 154 and male luer fitting 129 are shown to be mated by a friction fit, other matings between the luer fittings are possible. For example, male luer fitting 129 may have threads on the outside that have a corresponding threads on adapter 152. Thus, a threading engagement may mate pump unit 140 with phacoemulsification unit 110. In some instances, the pump unit 140 and phacoemulsification unit 110 may be coupled with both a friction fit and a threaded engagement. In particular implementations, pump unit 140 may be mated with phacoemulsification unit 110 through a threading engagement without a luer fitting. Various other couplings adapted to maintain phacoemulsification unit 110 and pump unit 140 in an integrated hand-held configuration during a procedure while still allowing decoupling are possible. Example couplings include a luer lock, a rotating thread cuff, and a barbed fitting into an elastomer.

Figure 2:
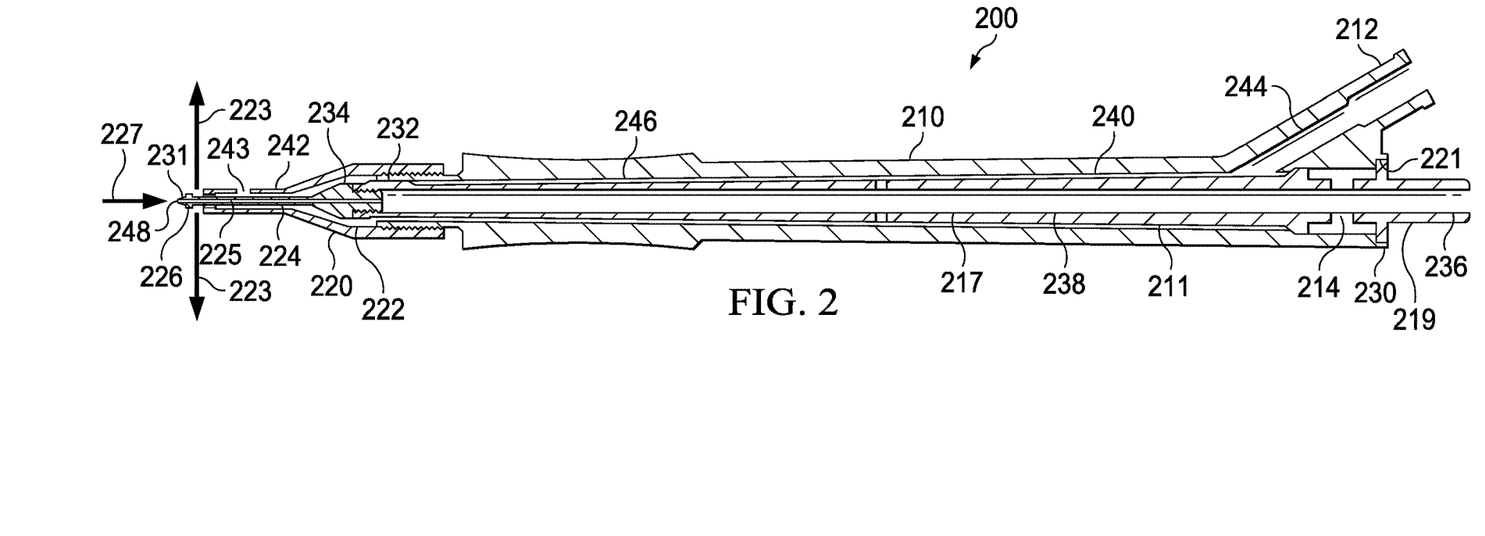
FIG. 2 is a cross-sectional view of an example irrigation-aspiration unit for ocular surgery.

FIG. 2 illustrates an example irrigation-aspiration ("I/A") unit 200. I/A unit 200 may, for example, be used with a pump unit similar to pump unit 140.

The example I/A unit 200 includes a housing 210 defining a channel 214, an insert 211 received within the channel 214, a male luer fitting 219 received in a recess 221 formed at a proximal end 230 of the housing 210, and a sleeve 220 coupled to a distal end 242 of the housing 210. The housing 210 may be formed from a rigid material. For example, the housing 210 may be formed from a rigid plastic, metal or other suitable material. The housing 210 also includes an infusion port 212 that defines a channel 244.

In some implementations, male luer fitting 219 is composed of a polymer. In other implementations, male luer fitting 219 may be composed of a metal or any other appropriate material.

The insert 211 defines a channel 217 extending therethrough. The male luer fitting 219 defines a channel 236. The I/A unit 200 also includes a cannula 224 extending from a distal end 232 of the insert 211. A proximal end 234 of the cannula 224 is received in the channel 217 at the distal end 232. The cannula 224 defines a channel 225 extending therethrough. The channels 217, 225 and 236 communicate with each other to define an aspiration passage 238.

The sleeve 220 defines a channel 222. The distal end of the housing 210 may be received into the channel 222, such that the sleeve 220 expands over the distal end of the housing 210 to form a sealed interface. In other implementations, other engagements (e.g., threaded or barbed) may be used. The cannula 224 extends through the channel 222 and such that a distal end 226 of the cannula 224 extends past a distal end 242 of the sleeve 220. In some instances, the cannula 224 may be formed entirely or in part from a plastic material. In other implementations, the cannula 224 may be formed from a metal, such as stainless steel or titanium. In other instances, the cannula 224 may be formed from any suitable material. Further, in some instances, the cannula 224 may include a tip 231. The tip 231 may be utilized, for example, to polish the capsular bag. In some instances, the tip 231 may be an integral part of the cannula 224. For example, where the cannula 224 is formed from a plastic, the tip 231 may be an integral part thereof. In implementations where the cannula 224 is formed from a metal, the tip 231 may be formed from a plastic applied to the distal end 226 of the cannula 224. For example, the tip 231 may be overmolded onto the cannula 224.

An outer surface of insert 211 and an inner surface of the housing 211 define an annular space extending 240 through the housing 210. The annular space 240 is isolated from the aspiration passage 238. The annular space 240 communicates with channels 222, 244 to define an infusion passage 246. The infusion passage 246 is fluidly separate from the aspiration passage 238.

Infusion fluid, such as a water/saline solution (e.g., a balanced salt solution), is introduced into the infusion passage 246 via the infusion port 212. In some implementations, the infusion fluid exits the I/A unit 200 at the distal end 242 of the sleeve 220, as indicated by arrows 223. In other implementations, the sleeve 220 may include one or more ports 243 formed at the distal end 242 thereof, which permit outflow of the irrigation fluid. The infusion fluid exits the I/A unit 200 at the distal end 242 of the sleeve 220, as indicated by arrows 223. The infusion fluid may be provided to an eye during a procedure, such as cortex removal or capsule polishing. The infusion fluid may, for example, be provided by a surgical console.

Aspirated materials, represented by arrow 227, are drawn into the aspiration passage 238 of the I/A unit 200 via a distal opening 248. The aspirated materials pass through the aspiration passage 238 and exit the I/A unit 200 via the male luer fitting 219.

In the illustrated implementation, sleeve 220 slideably engages with body portion 210. Thus, sleeve 220 expands over the distal portion of body portion 210 to create a sealed interface.

In operation, the I/A unit 200 may be coupled to a handheld pump unit, such as, for example, the pump unit 140, and to an irrigation supply line (e.g., from a surgical console). The distal end 226 of the cannula 224 may be inserted into the eye through an existing incision. Materials, such as cortical material, may then be aspirated, along with other tissue (e.g., epithelial cells), while leaving the posterior capsule intact. Simultaneously, fluids may be irrigated into the eye to stabilize it. Additionally, if desired, the posterior capsule of the eye may be polished with distal end 226.

The I/A unit 200 has a variety of features. For example, by locating a pump unit nearer to the phacoemulsification unit, chamber stability may be improved. Additionally, the I/A unit 200 may be used with a conventional surgical console if desired. A handheld pump unit can also be positioned remotely from the I/A unit 200 (e.g., for ergonomic reasons) and coupled to the irrigation-aspiration unit via aspiration tubing.

Although FIG. 2 illustrates an example I/A unit 200, other systems may use other I/A units that may include fewer, additional, and/or a different arrangement of components.

Figure 3A:
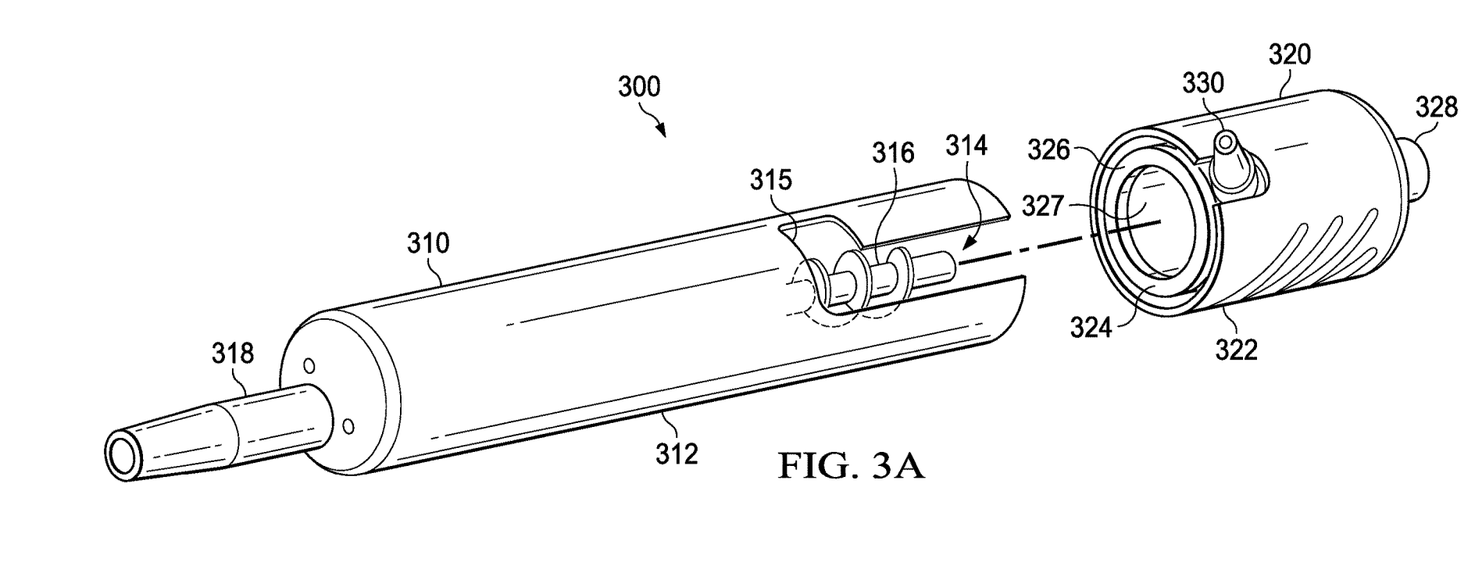
FIG. 3A shows a perspective view of an example pump unit for ocular surgery.
Figure 3B:
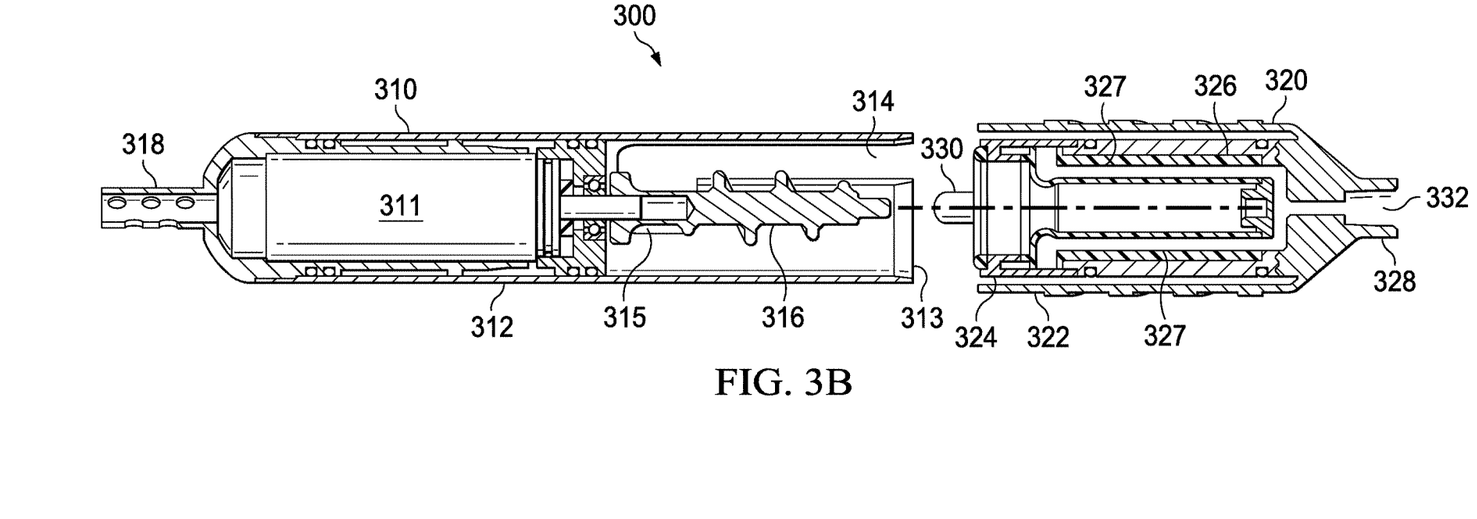
FIG. 3B is an exploded cross-sectional view of the example pump unit of FIG. 3A.

FIGS. 3A and 3B illustrate an example pump unit 300. Pump unit 300 includes a drive portion 310 and a pumping portion 320. Pump unit 300 may, for example, be usable in system 100.

Drive portion 310 includes a body 312. In the illustrated implementation, body 312 is generally cylindrical and made of metal, but may have other shapes and be made of other materials in other implementations. Body 312 includes a slot 314 configured to receive a fluid port 330 of pumping portion 320, to be discussed below. Inside body 312 is an electric motor and a rotor 316 that is driven thereby. A conduit 318 is used to supply electricity to drive portion 310.

Pumping portion 320 includes an outer shell 322 and an inner shell 324. Outer shell 322 is sized to fit around body 312 of drive portion 316 and inner shell 324 is sized to fit inside body 312. Thus, body 312 slides between outer shell 322 and inner shell 324. The shells 322, 324 may be made of hard plastic, metal, or any other appropriate material. Inside inner shell 324, pumping portion 320 includes an elastomeric pump segment 326 that includes integrated conduits 327. Elastomeric pump segment 326 engages rotor 316 in drive portion 310. The elastomeric pump segment 326 is engaged by the rotor 316 as the rotor 316 is rotated to cause material within the integrated conduits 327 to be transported therethrough. For example, the rotor 316 may compress the elastomeric pump section 326, thereby causing a peristaltic pumping action to transport material within the integrated conduits 327. Thus, elastomeric pump segment 326 may, for example, provide a peristaltic-type action to pump fluids through pump unit 300.

Pumping portion 320 also includes an adapter 328. In some instances, the adapter 328 may be adapted to engage a male luer fitting on a unit adapted to couple thereto (e.g., a phacoemulsification unit and/or an irrigation-aspiration unit). In other implementations, the adapter 328 may be adapted to be received into a female fitting on a unit, such as a phacoemulsification hand piece, and irrigation and aspiration hand piece, or any other desired device. Adapter 328 includes an interior channel 332. The interior channel 332 is in fluid communication with the integrated conduits 327. Fluid may be drawn into pump unit 300 through the interior channel 332. Pumping portion 320 also includes a fluid port 330 through which fluid may be expelled from pump unit 300. Fluid port 330 is sized to be received in slot 314 in body 312.

The drive portion 310 and the pumping portion 320 may be coupled together by insertion of a distal end 313 of the body 312 between the outer shell 322 and inner shell 324 of the pumping portion 320 with the fluid port 330 aligned with the slot 314. In the illustrated example, the pumping portion 320 may be rotated relative to the drive portion 310 such the fluid port 330 resides within a transverse portion 315 of the slot 314. Thus, by rotating the pumping portion 320 and drive portion 310 relative to each other, the fluid port 330 is made to reside in the transverse portion 315 of slot 314, causing the pumping portion 320 to be secured to drive portion 310.

Pump unit 300 has a variety of features. For example, pump unit 300 allows pumping action to be performed near a coupled unit, such as a phacoemulsification unit or irrigation-aspiration unit. Thus, chamber stability may be improved. Additionally, since pumping portion 320 is separable from drive portion 310, pumping portion 320 may be removed after a procedure (e.g., due to being contaminated with biological material) while preserving drive portion 310. Thus, drive portion 310 may be used for multiple procedures. Additionally, since adapter 328 is adapted to engage a number of coupleable units (e.g., a phacoemulsification unit, an irrigation-aspiration unit, etc.), pump unit 300 may be used for multiple operations during a surgical procedure.

Figure 4:
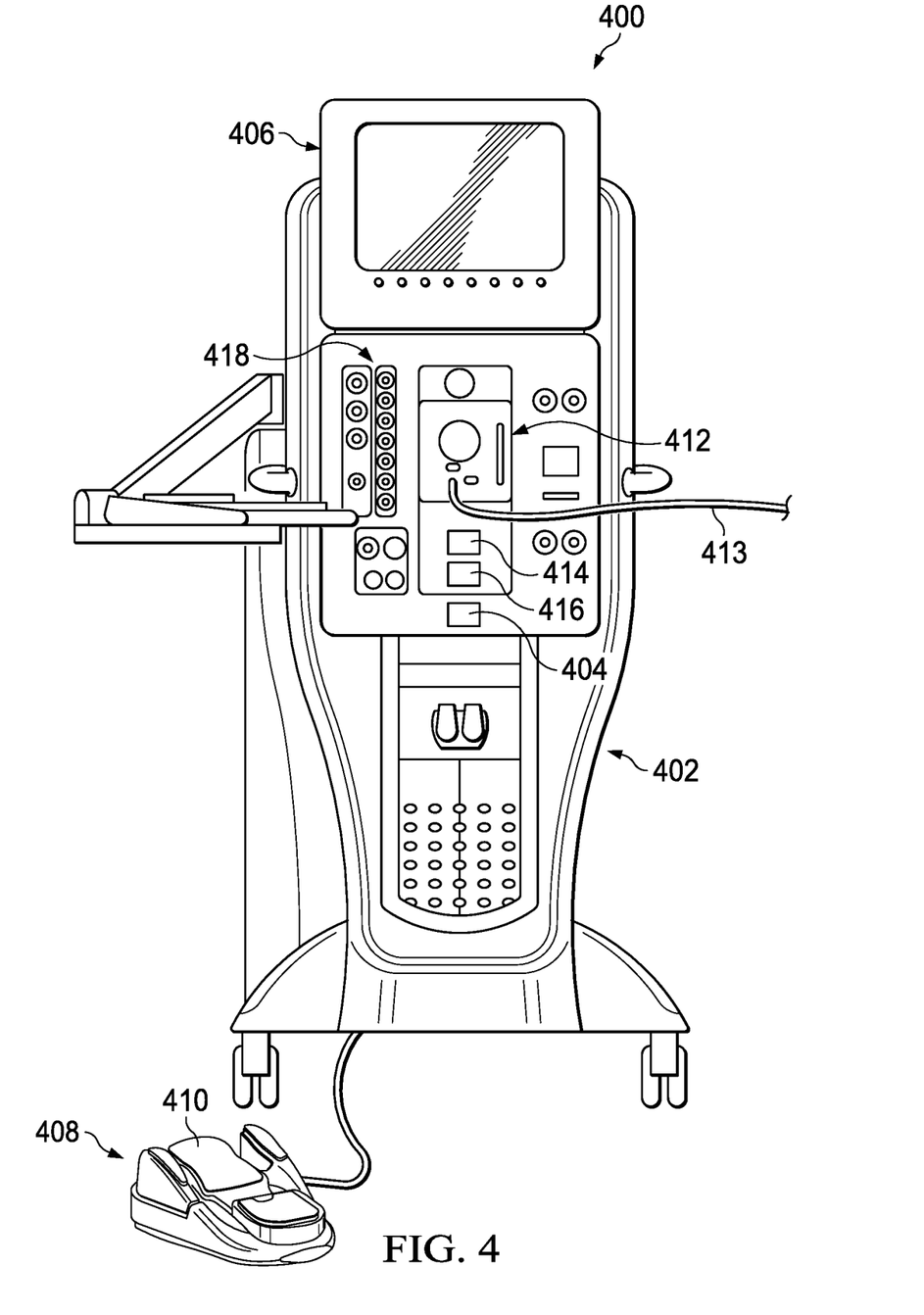
FIG. 4 shows an example surgical console for ocular surgery.

FIG. 4 illustrates an example surgical console 400 for use in ocular surgery. Console 400 includes a housing 402 with a computer system 404 and an associated display 406 operable to show, for example, data relating to system operation and performance during a surgical procedure. Display 406 may also interface with the console 400, such as to establish or change one or more operations of the console 400. In some instances, display 406 may include a touch-sensitive screen for interacting with the console 400 by touching the screen of the display 406.

Various probes may be used with surgical console 400. Console 400 may, for example, provide electrical, pneumatic, hydraulic, and/or other appropriate type of power to a probe. Console 400 may also be operable to control the supplied power, e.g., an infusion rate of fluid to a surgical site, aspiration of fluid from a surgical site, and/or ultrasonic power to a phacoemulsification unit, as well as to monitor one or more patient vital signs.

Console 400 may also include a number of systems that are used together to perform ocular surgical procedures. For example, the systems may include a footswitch system 408 including, for example, a footswitch 410, a fluidics system 412, which could, for example, provide active irrigation, aspiration, and a pneumatics system 418. The pneumatics system 418 may be operable to supply power to and control a probe. For example, the pneumatics system 418 may be operable to repeatedly cycle application of a pressurized gas. In some instances, the pneumatic system 418 may be operable to cycle pressurized gas at rates within the range of one cycle per minute to 7,500 cycles per minute, or possibly even 10,000 cycles per minute or more. In certain implementations, the cycled gas may be applied at, for example, different pressures, different rates, and different duty cycles. A probe may also be interfaced with console 400 via pneumatics system 418 (e.g., to control actuation of a cutter). Fluidics system 412 may be operable to provide infusion and/or irrigation fluids to the eye. The fluidics system 412 may also be operable to generate a vacuum, such as to aspirate materials during a surgical procedure. To optimize performance of the different systems during surgery, their operating parameters may be varied according to, for example, the particular procedure being performed, the different stages of the procedure, the surgeon's personal preferences, whether the procedure is being performed in the anterior or posterior portion of the patient's eye, and so on.

In this implementation, fluidics system 412 includes a fluid reservoir 414 and a fluid control device 416. Fluid reservoir 414 holds the fluid to irrigate an eye. The fluid may, for example, be a water/saline solution. In particular implementations, fluid reservoir 414 may also supply fluid for other operations during an ocular surgery (e.g., to maintain intraocular pressure). Fluid control device 416 is coupled to fluid reservoir 414 and is adapted to control the flow of fluid from fluid reservoir 414 to an irrigation port of a handheld device (e.g., a phacoemulsification probe or an irrigation-aspiration probe). Fluid reservoir 414 may, for example, be a bag, and fluid control device 416 may be a pump. Fluidics system 412 may also supply the irrigation fluid by a gravity feed.

The different systems in console 400 may include control circuits for the operation and control of the various functions and operations performed by console 400, such operations of a probe. Computer system 404 may be operable to govern the interaction and relationship between the different systems to properly perform a surgical procedure. To do this, computer system 404 may include one or more processors, one or more memory devices, and may be configured or programmed to control operations of console 400, for example, based upon pre-established programs or sequences.

In certain modes of operation, console 400 may provide irrigation fluid to a phacoemulsification unit through a line 413. The phacoemulsification unit may receive suction for aspiration from a local pump unit that is coupled to the phacoemulsification unit. The console may also supply irrigation fluid to another coupleable unit (e.g., an irrigation-aspiration unit) through line 413. Further, one unit, e.g., the irrigation-aspiration unit, may be utilized subsequent to a previously used unit, e.g., a phacoemulsification unit. However, a unit, such as one or more of the units described herein or other suitable units, may be used in any desired order. The irrigation-aspiration unit may also receive suction from the pump unit, which may have been previously coupled to the phacoemulsification unit.

In certain implementations, console 400 may provide suction for one or more handpieces. For example, console 400 could provide suction for a phacoemulsification unit of an I/A unit. In some instances, the console 400 may be used to provide suction to an I/A unit such as I/A unit 200.

Figure 5:
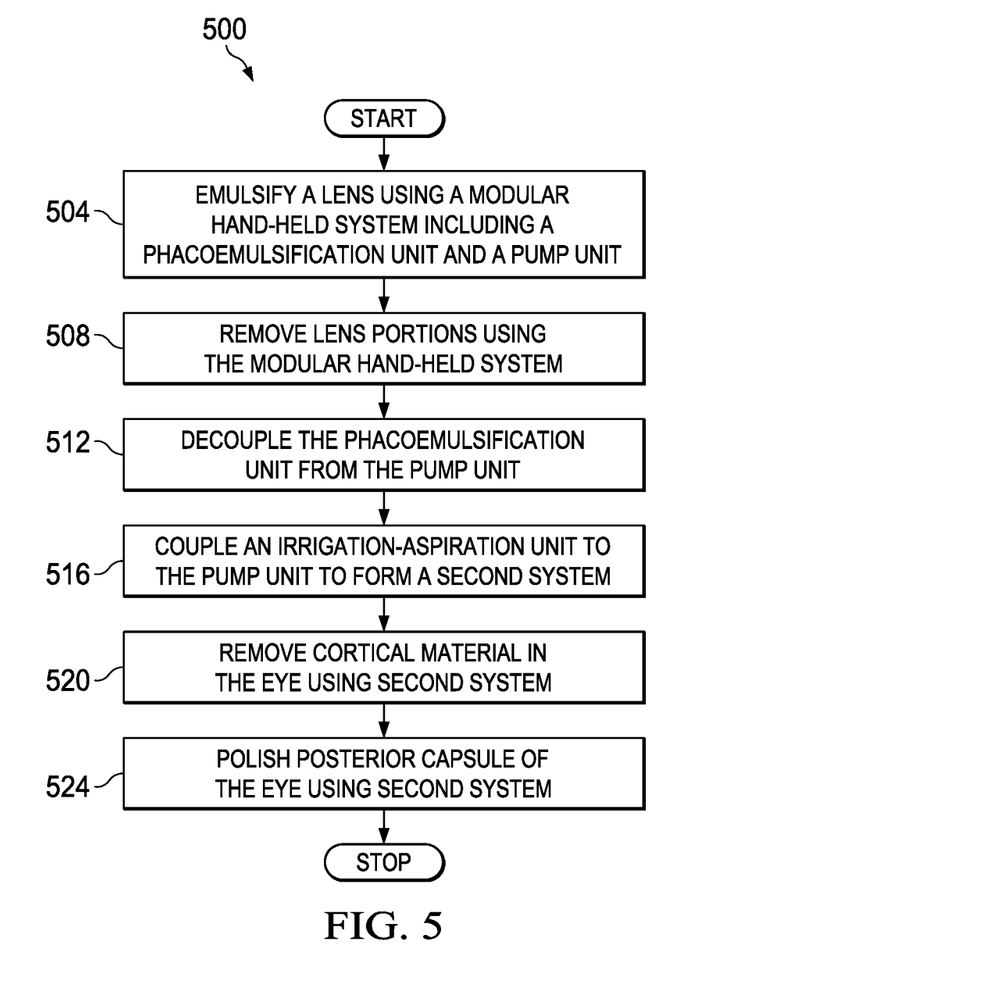
FIG. 5 is a flowchart illustrating an example process for ocular surgery.

FIG. 5 illustrates selected operations for an example process 500 for ocular surgery. Process 500 may, for example, be accomplished with a system similar to system 100.

Process 500 calls for emulsifying a lens in an eye using a modular hand-held system including a phacoemulsification unit and a pump unit (operation 504). Emulsifying a lens, may, for example, include breaking the lens into several pieces using ultrasonic movement. For example, in some instances, the lens may be fragmented into four pieces. However, the lens may be fragmented into any number of different pieces.

Process 500 also calls for removing portions of the lens using the hand-held system (operation 508). For example, portions of the lens may be aspirated out through the phacoemulsification unit due to suction provided by the pump unit.

Process 500 additionally calls for decoupling the phacoemulsification unit from the pump unit (operation 512). The phacoemulsification unit may, for example, be decoupled by detaching a male luer fitting of the phacoemulsification unit from a female luer fitting of the pump unit.

Process 500 also calls for coupling an irrigation-aspiration unit to the pump unit to form a second system (operation 516). The irrigation-aspiration unit may, for example, be coupled by attaching a male luer fitting of the irrigation-aspiration unit to a female luer fitting of the pump unit.

Process 500 additionally calls for removing materials from the eye using the second system (operation 520). For example, cortical materials may be removed from the eye. Other materials, e.g., fluids and/or other tissues, may also be removed. The materials may, for example, be removed by being aspirated out through the irrigation-aspiration unit due to suction provided by the pump unit.

Process 500 also calls for polishing the lens capsule of the eye with the second system (operation 524). The posterior capsule may, for example, be polished with a tip or distal end of the irrigation-aspiration unit.

Although FIG. 5 illustrates one implementation of a process for ocular surgery, other processes for ocular surgery may include fewer, additional, and/or a different arrangement of operations. For example, a process may include operations prior to emulsifying the lens. For instance, one or more incisions may be made in the eye (e.g., through the cornea) to allow the introduction of surgical instruments. Also, the anterior face of the capsule that contains the lens inside the eye may be removed. As an additional example, a process may include irrigating the eye (e.g., with a balanced salt solution) during the removal of the lens and/or other materials from the eye. As another example, a process may not include polishing the lens capsule. As a further example, a process may include switching an irrigation supply line from the phacoemulsification unit to a separate irrigation handpiece unit. Moreover, a number of the operations may be performed in a contemporaneous or simultaneous manner.

The various implementations discussed and mentioned herein have been used for illustrative purposes only. The implementations were chosen and described in order to explain the principles of the disclosure and the practical application and to allow those of skill in the art to understand the disclosure for various implementations with various modifications as are suited to the particular use contemplated. Thus, the actual physical configuration of components may vary. For example, the mentioned size(s) of components and their illustrated sizing relative to each other may vary based on application. Moreover, the shapes of one or more components may vary depending on application. Thus, the illustrative implementations should not be construed as defining the only physical size, shape, and relationship of components.

Various systems and techniques for ocular surgery have been discussed, and several others have been mentioned or suggested. However, those skilled in the art will readily recognize that a variety of additions, deletions, substitutions, and modifications may be made to these systems and techniques while still achieving ocular surgery. Thus, the scope of protection should be judged based on the following claims, which may capture one or more aspects of one or more implementations.

The invention claimed is:

1. A hand-held pump unit comprising:
   a pumping portion comprising:
      an adapter disposed at a distal end of the pumping portion and configured to detachably couple a surgical instrument to the pump unit to form an integrated hand-held system, the adapter defining an interior channel, the interior channel defining a fluid flow path; and
      an elastomeric pump segment disposed within the pumping portion and defining a cavity, the elastomeric pump segment forming integrated compressible conduits disposed about a circumference of the pumping portion and in fluid communication with the interior channel and laterally offset therefrom, the compressible conduits extending longitudinally along the pumping portion and dividing the fluid flow path of the interior channel into separate fluid flow paths; and
   a drive portion removably couplable to the pumping portion, the drive portion comprising:

a body;

a motor disposed within the body; and a rotor coupled to the motor and rototable thereby, the rotor receivable into the cavity and adapted to compress each of the compressible conduits to peristaltically pump a separate fluid flow within each of the compressible conduits as the rotor rotates.

2. The system of claim 1, wherein the pumping portion further comprises a fluid port through which the separate fluid flow paths within the compressible conduits are expelled from the pump unit.

3. The system of claim 2, wherein the body comprises a slot configured to receive the fluid port when the pumping portion couples to the drive portion.

4. The system of claim 3, wherein the slot comprises a transverse portion, and wherein the fluid port is made to reside within the transverse portion by rotation of the pumping portion relative to the drive portion.

5. The system of claim 1, wherein the pumping portion comprises an outer shell and an inner shell, wherein the outer shell is sized to fit around the body and wherein the inner shell is sized to fit inside the body when the pumping portion is coupled to the drive portion.

6. The system of claim 1, wherein the rotor comprises a helical scroll.

7. The system of claim 6, wherein the helical scroll compresses the compressible conduits.

8. The system of claim 1, wherein the interior channel is centrally located along a longitudinal axis of the pumping portion.

9. The system of claim 1, wherein the pumping portion further comprises a recess configured to receive a distal end of the rotor.

10. The system of claim 9, wherein the recess is centrally located along a longitudinal axis of the pumping portion.

* * * * *